US012419530B2

(12) United States Patent
Osteyee et al.

(10) Patent No.: US 12,419,530 B2
(45) Date of Patent: Sep. 23, 2025

(54) SENSOR-ENABLED TAMPER-RESISTANT BODY-WORN MONITORING CUFF

(71) Applicant: 4Sight Labs Inc., San Francisco, CA (US)

(72) Inventors: Ian Andrew Osteyee, Keene, NY (US); John Anthony Defalco, San Francisco, CA (US)

(73) Assignee: 4Sight Labs Inc., San Francisco, CA (US)

( * ) Notice: Subject to any disclaimer, the term of this patent is extended or adjusted under 35 U.S.C. 154(b) by 320 days.

(21) Appl. No.: 18/122,439

(22) Filed: Mar. 16, 2023

(65) Prior Publication Data

US 2023/0293034 A1 Sep. 21, 2023

Related U.S. Application Data

(60) Provisional application No. 63/373,069, filed on Aug. 21, 2022, provisional application No. 63/322,464, filed on Mar. 22, 2022, provisional application No. 63/320,554, filed on Mar. 16, 2022.

(51) Int. Cl.
| | |
|---|---|
| *A61B 5/024* | (2006.01) |
| *A61B 5/00* | (2006.01) |
| *A61B 5/0205* | (2006.01) |
| *G08B 3/10* | (2006.01) |

(52) U.S. Cl.
CPC ...... *A61B 5/02438* (2013.01); *A61B 5/02055* (2013.01); *A61B 5/746* (2013.01); *G08B 3/10* (2013.01)

(58) Field of Classification Search
CPC ............ A61B 5/02438; G08B 21/0211; G08B 21/0286; G08B 21/0288
See application file for complete search history.

(56) References Cited

U.S. PATENT DOCUMENTS

| | | | |
|---|---|---|---|
| 5,191,891 | A | 3/1993 | Righter |
| 11,434,668 | B1 | 9/2022 | Wriggle |
| 2007/0027386 | A1 | 2/2007 | Such |
| 2007/0096897 | A1 | 5/2007 | Weiner |

(Continued)

FOREIGN PATENT DOCUMENTS

| | | |
|---|---|---|
| CN | 105931433 A | 9/2016 |
| CN | 106014014 A | 10/2016 |

(Continued)

*Primary Examiner* — James M Kish
*Assistant Examiner* — James Moss
(74) *Attorney, Agent, or Firm* — Young Basile Hanlon & MacFarlane, P.C.

(57) ABSTRACT

A sensor-enabled tamper-resistant body-worn monitoring cuff that includes a magnet and a magnetic sensor that are adjacent to each other when the cuff is worn by an individual and are separated when the cuff is removed. The magnetic sensor detects a magnetic field of the magnet and causes an alert message to be wirelessly transmitted when the magnetic field drops below a predetermined threshold. The cuff further includes a physiological sensor, such as a heartrate sensor, and an inertial sensor, such as an accelerometer, which detect signals that are analyzed to determine whether the individual's physiological parameters have deviated from normal or expected values and which may cause an alert message to be wirelessly transmitted.

20 Claims, 6 Drawing Sheets

(56) References Cited

U.S. PATENT DOCUMENTS

| | | | |
|---|---|---|---|
| 2009/0265971 A1* | 10/2009 | Cook | G09F 3/005 |
| | | | 224/267 |
| 2014/0340217 A1 | 11/2014 | Moenning | |
| 2014/0343391 A1 | 11/2014 | Korkala | |
| 2016/0089081 A1 | 3/2016 | Morris | |
| 2017/0084150 A1* | 3/2017 | Keyton | G08B 21/0261 |
| 2019/0304283 A1* | 10/2019 | Carr | A41F 9/00 |
| 2020/0029840 A1 | 1/2020 | Nguyen | |
| 2022/0192568 A1 | 6/2022 | Lee | |
| 2022/0207635 A1 | 6/2022 | Hughes | |
| 2022/0287576 A1 | 9/2022 | Little | |

FOREIGN PATENT DOCUMENTS

| | | |
|---|---|---|
| CN | 112471712 A | 3/2021 |
| WO | 22201080 A1 | 9/2022 |

* cited by examiner

SENSOR-ENABLED TAMPER-RESISTANT BODY-WORN MONITORING CUFF

CROSS-REFERENCE TO RELATED APPLICATIONS

This patent application claims priority benefit under 35 U.S.C. § 119(e) of U.S. Provisional Patent Applications, Ser. No. 63/320,554, filed Mar. 16, 2022, Ser. No. 63/322,464, filed Mar. 22, 2022, and Ser. No. 63/373,069, filed Aug. 21, 2022, the disclosures of which are incorporated by reference herein in their entirety.

FIELD

This disclosure relates to devices for law enforcement, and more particularly, to locking bands and cuffs that include electronics for monitoring physiological signals and physical movements of a person wearing the cuff, for wirelessly transmitting physiological and movement information and/or alert messages to a receiving device, and for detecting tampering with or removal of the cuff from the individual. Even more particularly, this disclosure relates to a wrist (arm) or ankle (leg) cuff comprising a heartrate sensor for monitoring electrical heart activity, an accelerometer for monitoring physical movements, a magnetometer for monitoring removal activity, and a wireless communications module for sending alerts, sensor data, or related information to an electronic device.

BACKGROUND

One aspect of law enforcement activities is to monitor an individual, for example, if the individual is in custody, has been detained (e.g., in jail or prison), is under house arrest, or has been released on personal recognizance. Monitoring may include tracking the individual's geographic or spatial location, his physical movements or activities, and/or certain physiological parameters. While visually monitoring the individual can be useful, it is not always practical. Thus, there is a need for monitoring cuffs (bracelets, anklets, bands, and so on) that may be secured to the individual to help perform monitoring functions remotely.

Monitoring physiological parameters may be especially important because: (1) the individual may have preexisting physical or mental conditions that could be triggered or exacerbated from stress or physical exertions; (2) the individual may have been physically injured in connection with being detained, restrained, and/or monitored; or (3) the individual may experience anxiety, distress, agitation, or other emotions as a result of being detained, restrained, and/or monitored. Such physical, mental, and/or emotional states may result in divergent physiological conditions of the individual, such as elevated or irregular heart rate or elevated blood pressure, that may cause additional injury or even death of the individual. It is therefore beneficial to be able to continuously or frequently monitor certain physiological conditions of the individual and to receive notifications when such physiological conditions exceed certain thresholds or exhibit certain patterns. Because the individual may be uncooperative, it is additionally beneficial to be able to detect if the individual attempts to remove or otherwise tamper with a monitoring cuff that the individual may be required to wear.

While much of the descriptions herein focus on individuals who may involuntarily wear a monitoring cuff (e.g., as required by law enforcement), there are also individual who may voluntarily wear such a monitoring cuff, such as military personnel, police officers, industrial workers, hikers, and so on.

SUMMARY

The disclosed embodiments provide for a body-worn cuff that includes a sensor for monitoring certain physiological conditions of an individual wearing the cuff, an inertial sensor for monitoring certain movements of the individual, and a magnetic sensor, in association with a magnet, for determining whether the cuff has been removed from the individual. The physiological sensor, such as a heartrate sensor, and the inertial sensor, such as an accelerometer, detect signals that are analyzed to determine whether the individual's physiological parameters have deviated from normal or expected values, which may cause an alert message to be wirelessly transmitted. The magnetic sensor detects a magnetic field of the magnet and causes an alert message to be wirelessly transmitted when the magnetic field drops below a predetermined threshold.

In one embodiment, the cuff comprises:
a strap comprising a first end extending from a medial section opposite a second end and a third end, wherein the second end and the third end at least partially overlap;
a catch protruding from a plane of the first end and adapted for insertion through at least one slot in the second end and at least one slot in the third end;
a housing disposed on the second end that houses an electronics system; and
a magnet disposed on the third end adjacent to the housing.

In some embodiments, the electronics system comprises: a battery; a processor; a wireless transceiver; an antenna; and a magnetic sensor; wherein processor is configured to cause the wireless transceiver to transmit an alert message via the antenna in response to the magnetic sensor having detected a magnetic field of the magnet that is below a magnitude-threshold.

In some embodiments, the electronics system further comprises: a physiological sensor configured to detect physiological data of an individual wearing the cuff; and an inertial sensor configured to collect movement data of the individual wearing the cuff.

In some embodiments, the cuff further comprises: a tamper-resistant lock adapted to mechanically couple to the catch having been inserted through at least one slot in the second end and at least one slot in the third end.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings.

DETAILED DESCRIPTION

The present disclosure may be more readily understood by reference to the following detailed description and the accompanying drawings, which form a part of this disclosure. This disclosure is not limited to the specific devices, methods, conditions, or parameters described and/or shown herein, and the terminology used herein is for the purpose of describing particular embodiments by way of example only and is not intended to be limiting of disclosed embodiments or inventions. For example, "left," "right," "clockwise," and "counterclockwise" may be used as specific examples of generally opposite lateral or rotational directions, respectively. Also, as used in the specification and including the appended claims, the singular forms "a," "an," and "the" include the plural, and reference to a particular numerical value includes at least that particular value, unless the context clearly dictates otherwise.

The following numerals are used to describe various features of the embodiments.

| | |
|---|---|
| 10 | cuff |
| 20 | catch |
| 30 | lock |
| 100 | medial section |
| 110 | first end |
| 120 | second end |
| 125 | slot |
| 130 | third end |
| 135 | slot |
| 200 | housing |
| 210 | electronics system |
| 220 | magnetic sensor |
| 230 | physiological sensor |
| 240 | inertial sensor |
| 250 | processor |
| 260 | battery |
| 270 | power controller |
| 280 | wireless transceiver |
| 290 | antenna |
| 300 | magnet |
| 400 | electronic device |
| 460 | wireless channel |
| 470 | receiving device |
| 480 | gateway device |

Figure 1:
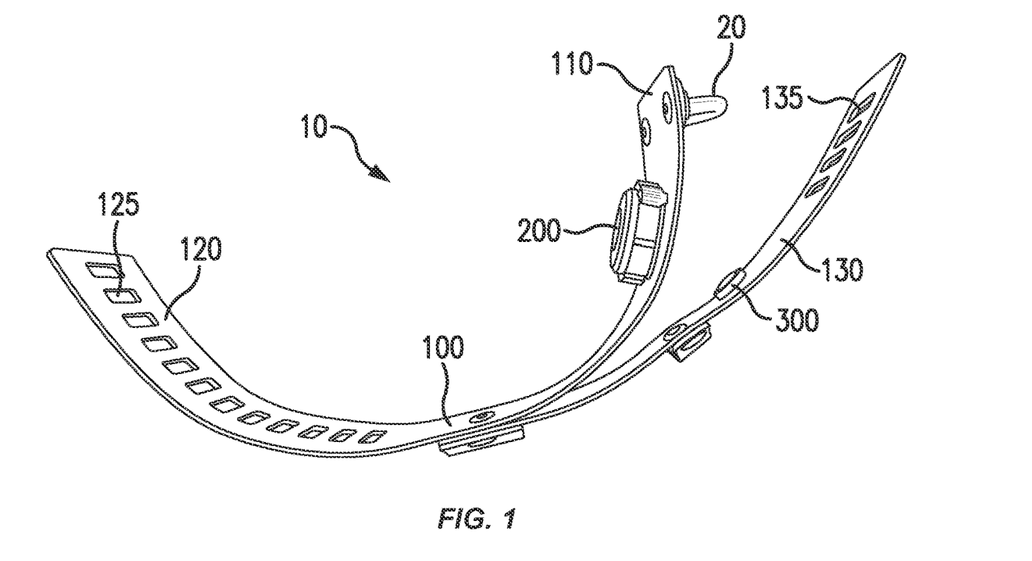
FIG. 1 shows an embodiment of the monitoring cuff in a fully opened position, i.e., fully disengaged.

FIG. 1 shows an embodiment of the monitoring cuff 10 in a fully opened position, i.e., fully disengaged. A cuff may also be referred to as a band, strap, bracelet, anklet, and so on. The cuff 10 comprises a strap-like medial section 100 and three strap-like distal sections, a first end 110, a second end 120, and a third end 130. The first end 110 extends from the medial section 100 opposite from the second end 120 and the third end 130. The second end 120 and the third end 130 at least partially overlap. The medial section 100, the first end 110, the second end 120, and the third end 130 independently comprise any sufficiently durable materials and methods of construction, such as rubber, synthetic rubber, silicone, polyamide (Nylon), woven fabric, webbing, leather, metal, and so on.

Figure 2:
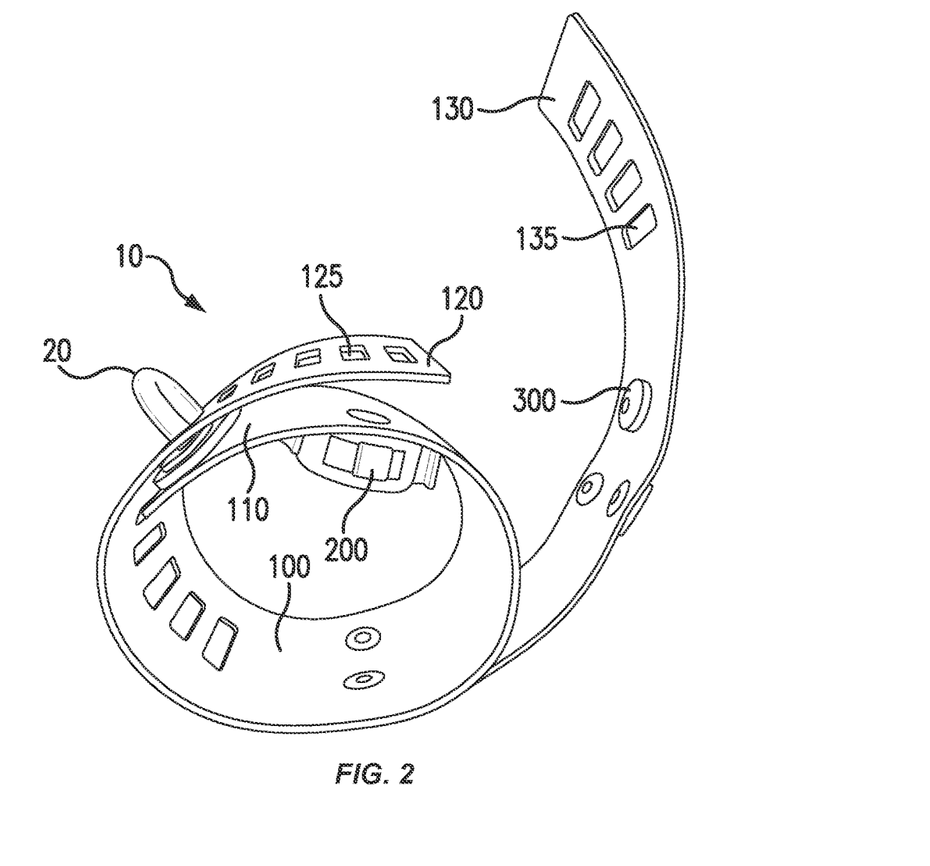
FIG. 2 shows an embodiment of the monitoring cuff in a partially closed position, i.e., partially engaged.
Figure 3:
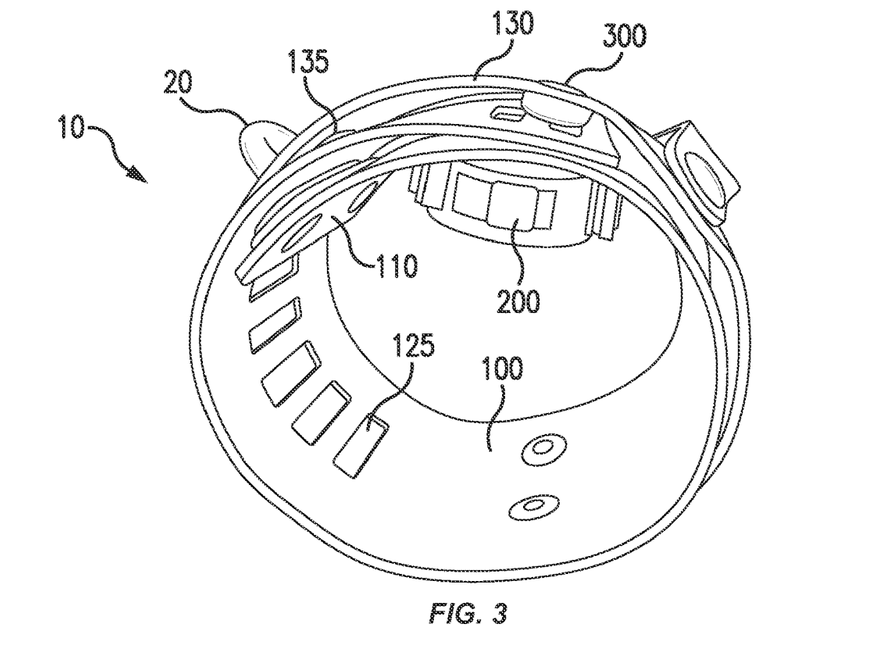
FIG. 3 shows an embodiment of the monitoring cuff in a fully closed position, i.e., fully engaged.
Figure 4:
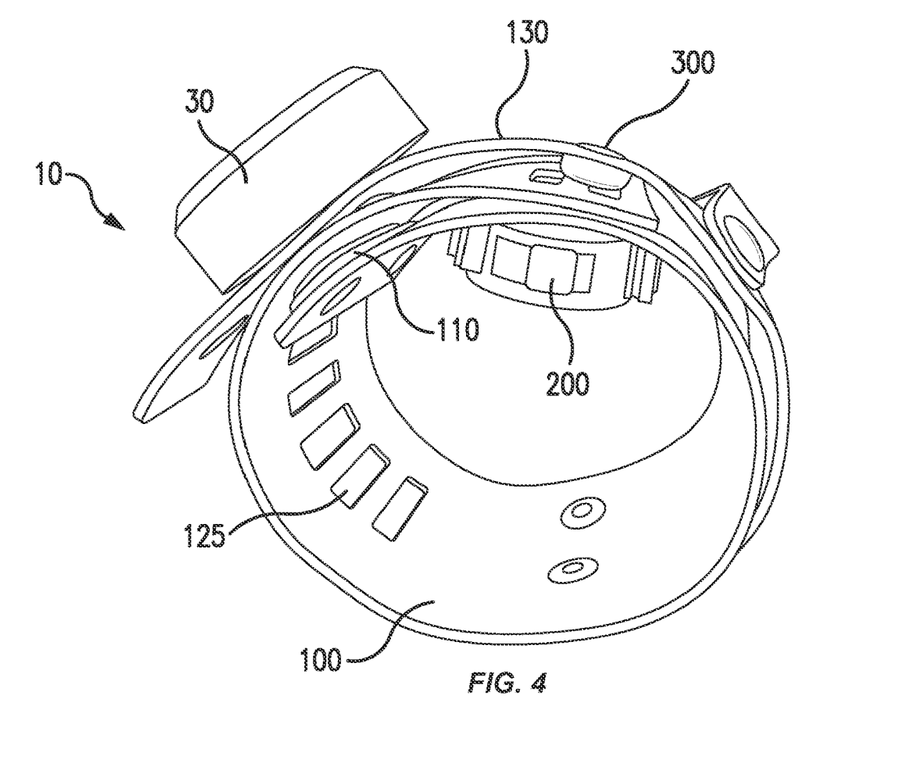
FIG. 4 shows an embodiment of the monitoring cuff in a fully closed position, i.e., fully engaged, and locked.
Figure 8:
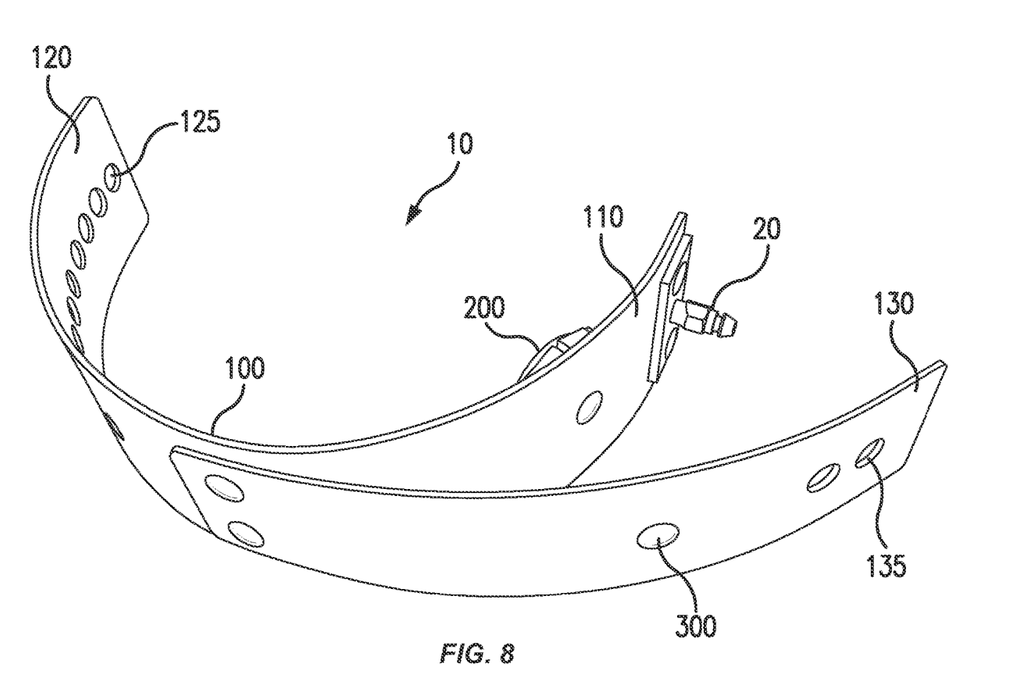
FIG. 8 shows an alternate embodiment of the monitoring cuff in a fully opened position, i.e., fully disengaged.

Each of the second end 120 and the third end 130 include slots 125 and slots 135, respectively, adapted to engage with a catch 20 that extends from a plane of the first end 110. Each slot 125 and each slot 135 is an aperture or opening that may assume any suitable shape, for example, elongated, round, rectangular, square, and so on. FIG. 2 shows the cuff 10 in a partially closed position, i.e., partially engaged, where the first end 110 is engaged with the second end 120 via the catch 20 having been inserted through one of the slots 125. FIG. 3 shows the cuff 10 in a fully closed position, i.e., fully engaged, where the first end 110 is engaged with the third end 130 via the catch 20 having been inserted through one of the slots 135. The catch 20 may be a loop, ring, pad eye, eyelet, post, pin, stud, boss, or any other suitable member capable of engaging with the slots 125 and the slots 135. FIG. 8 shows an embodiment of the cuff 10 where the catch 20 comprises a post and slots 125 and slots 135 are each round holes. In some embodiments, in lieu of a catch 20 engaging with slots 125 and slots 135, the first end 110 may engage with the second end 120 via hook-and-loop fasteners, magnets, clasps, snaps, buttons, adhesive, and so on. Similarly, the second end 120 may engage with the third end 130 via hook-and-loop fasteners, magnets, clasps, snaps, buttons, adhesive, and so on.

In the fully engaged position shown in FIG. 3, the second end 120 is sandwiched between the first end 110 and the third end 130. If the catch 20 has been inserted through a slot 125 that is near the median section 100, the circumference of the fully engaged cuff 10 is smaller than if the catch 20 had been inserted through a slot 125 further from the medial section 100. Thus, the fit of the cuff 10 around an individual's arm or leg may be adjusted based on which slot 125 of the second end 120 is utilized. In other words, selection of the slots 125 of the second end 120 determines a majority of the tightness or looseness of the cuff 10. While the third end 130 may comprise multiple slots 135, selection of which slot 135 to engage with the catch 20 may not have as significant a role in determining the tightness or looseness of the cuff 10.

To prevent the fully engaged cuff 10 from disengaging, a lock 30 may be coupled to the catch 20. The lock 30 may comprise any suitable mechanism, such as a padlock, knob lock, cable lock, cam lock, mortise lock, cylinder lock, deadbolt, and so on, and/or it may comprise any suitable member, such as a cable tie, a crimped cable, a lock ring, and so on.

As shown in FIGS. 1-4, a magnet 300 may be disposed on the third end 130. The magnet 300 may be affixed to or integrated within the third end 130 via any suitable means, such as with adhesive, glue, tape, threaded stitching, molded-in-place, press-fit, and so on. When the cuff 10 is in a fully engaged position, the magnet 300 may align with a magnetic sensor 220 (depicted in FIG. 5) that is housed within a housing 200 disposed on the first end 110. Because the first and 110 and the third end 130 extend from a same end of the medial section 100, the magnet 300 and the magnetic sensor 220 will always approximately line up regardless of which slot 125 of the second end 120 is engaged with the catch 20 when the cuff 20 is worn.

A purpose of the magnet 300 and magnetic sensor 220 is to detect whether the fully engaged and locked cuff 10 that is worn by an individual has been removed, i.e., disengaged. The magnetic sensor 220 detects the magnetic field of the magnet 300, where the magnetic field strength detected by the magnetic sensor 220 is directly proportion to the proximity of the magnet 300 thereto. The magnetic sensor 220 may be any suitable type of sensor or sensors capable of detecting the magnetic field of the magnet 300, for example, a hall effect sensor, a reed switch, a magnetoresistive element, and so on. A magnetic sensor may sometimes be referred to as a magnetometer. When the magnet 300 is within a certain proximity of the magnetic sensor 220, the magnitude of the detected magnetic field is above a predetermined lower threshold; as the magnet 300 moves away from the magnetic sensor 220, the magnitude of the detected magnetic field decreases until it falls below the predetermined lower threshold, which may indicate that the worn cuff 10 has been removed.

In some embodiments, a predetermined upper threshold may be utilized. For example, the magnetic sensor 220 detecting magnetic field magnitude above the predetermined upper threshold may indicate that another magnet has been brought near the cuff 10, perhaps being used as a decoy magnet while the cuff 10 is being disengaged and the magnet 300 is being separated from the magnetic sensor 220.

One benefit of using a magnetic sensor 220 and magnet 300 for detecting whether the cuff 10 has been disengaged is that the magnetic sensor 220 and magnet 300 need not be in physical and continuous contact with each other. For example, an electrical contact sensor relies on a continuous electrically conductive connection between electrical contacts. However, movement of the individual wearing the cuff 10 may cause intermittent disconnections between the contacts, which could trigger false alerts that the cuff 10 has been disengaged. Further, electrical contacts may be susceptible to corrosion, which could negatively affect an electrical contact sensor's reliability.

Figure 5:
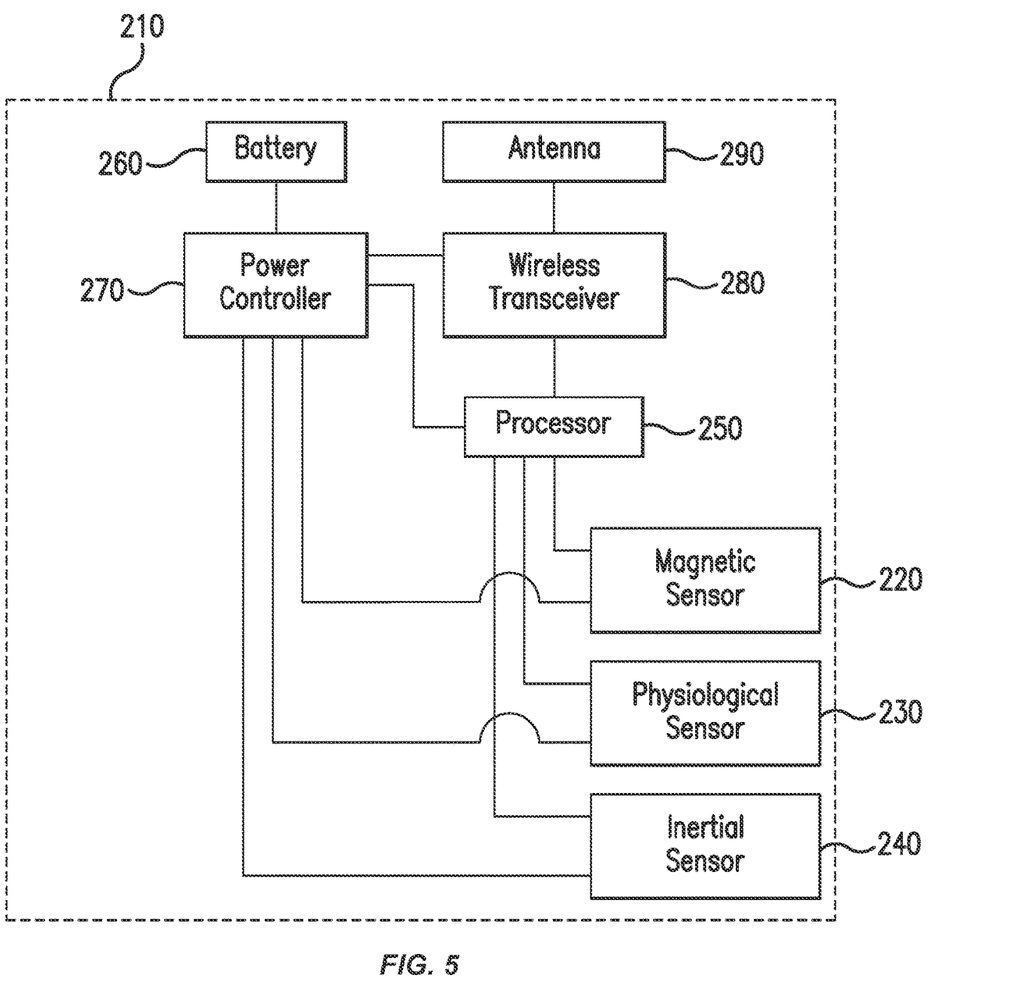
FIG. 5 shows several components of an electronics system of an embodiment of the monitoring cuff.

FIG. 5 shows an exemplary electronic system 210 that may be housed within the housing 200. In some embodiments, some of the electronic components shown in FIG. 5 may be external to the housing 200. In some embodiments, the housing 200 may be modular and removeable and/or replaceable. The electronics system 210 may include a battery 260 for providing power to the electrical components, where the battery 260 may be single-use or rechargeable, and may be integral or replaceable. A rechargeable battery 260 may be recharged by any suitable means, such as non-contact inductive charging. The battery 260 may be coupled to a power controller 270 that controls and manages electrical voltages and/or currents within the electronics system 210. A processor 250 may be any suitable electronic component capable of executing instructions, such as a microprocessor, a microcontroller, an application-specific integrated circuit (ASIC), a field-programmable gate array (FPGA), and so on. The processor 250 is coupled to the magnetic sensor 220, to a physiological sensor 230 (described further below), and to an inertial sensor 240 (described further below). The processor 250 may receive and process signals from these sensors and interface with a wireless transceiver 280 to transmit alerts, processed data, and/or raw data to an electronic device 400 via an antenna 290. The processor 250 may also receive information via the antenna 290 and the wireless transceiver 280, for example, to update firmware or software or to upload analytical models for the sampling, analysis, and/or processing of sensor data. The processor 250 may utilize such analytical models to determine appropriate thresholds for creating or sending of alert messages (described further below). An alert that is based on a received alert message may take any suitable form, such as stimulus produced by an electronic device that received the alert message, which may be visual (e.g., graphics and/or text on a display screen or flashing lights), audible (e.g., bells or sirens), or tactile (e.g., vibrations of a wristwatch/smartwatch). The terms "notification" and "alert" may be used interchangeably herein. Further, the cuff 10 may itself generate visual, audible, or tactile alerts instead or in addition to transmitting an alert message.

The physiological sensor 230 may comprise any suitable types of sensors to detect relevant physiological data of an individual wearing the cuff 10, for example: electrocardiogram heart-rate sensors (EKG; also abbreviated ECG) that detect electrical activity of the heart; photoplethysmography (optical) sensors that may detect changes in volume of a blood vessel; pulse oximetry sensors (optical) that may detect blood oxygen saturation levels; temperature sensors (e.g., thermocouples, resistance temperature detectors (RTDs), thermistors, etc.) that may detect a body temperature; and so on.

The inertial sensor 240 may comprise any suitable types of sensors to detect relevant inertial data of an individual wearing the cuff 10, for example: accelerometers and gyroscopes (e.g., micro-electromechanical systems (MEMS)) that may detect various types of motions and orientations; global positioning sensors (GPS) that may utilize ground-based and satellite transmissions to determine an absolute global position; and so on.

Figure 6:
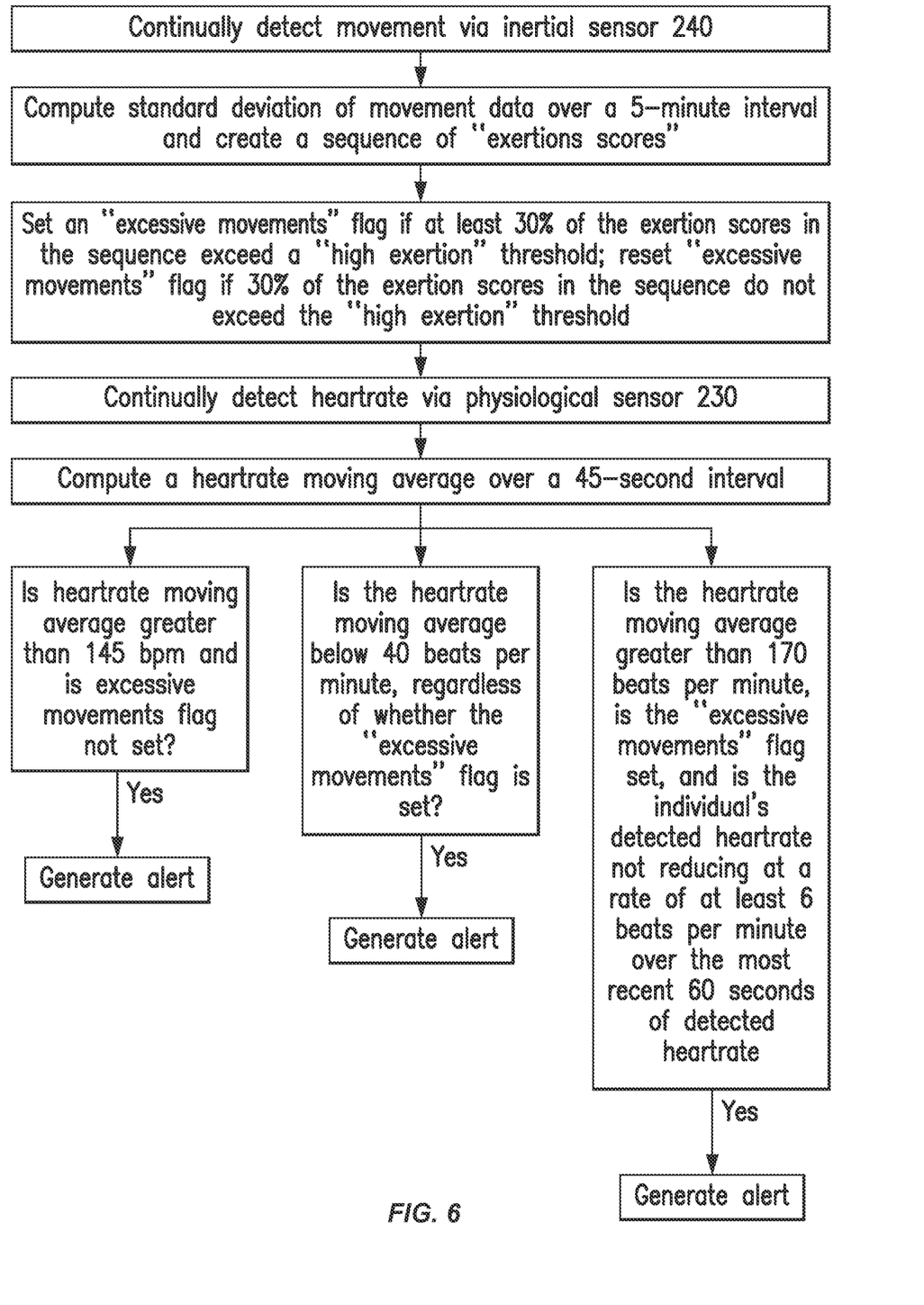
FIG. 6 shows a flowchart of an exemplary process for generating an alert based on inertial and physiological sensor data.

Data collected by the physiological sensor 230 and the inertial sensor 240 may be processed, by software or firmware instructions executing on the processor 250, independently or as a sensor-fused system. In one embodiment, the data is processed as a sensor-fused system as described below and as shown in FIG. 6.

(1) The processor 250 executes instructions for continually receiving and analyzing data collected by an accelerometer inertial sensor 240 to quantify a level (or levels) of physical exertion of an individual wearing the cuff 10 over a given interval. In some embodiments, "continually" means as frequently as possible for a specific processor 250, which may be determined by a synchronous clock rate, a signal sampling rate, and so on. In some embodiments, "continually" relates to the interval under consideration, for example, receiving and analyzing data at least several times per minute over a one-minute interval, at least several times per second over a one-second interval, and so on. The level of physical exertion may be determined by calculating a standard deviation across a series of readings of an accelerometer inertial sensor 240 and creating an "exertion score" that describes how much the individual appears to be moving. The processor 250 may store in memory a sequence of exertion scores over an interval of interest and may characterize the sequence as a baseline pattern. The processor 250 may set an "excessive movements" flag if a certain quantity or percentage of exertion scores in the interval of interest exceed a predetermined "high exertion" threshold. In some embodiments, the interval of interest is five minutes, and the "excessive movements" flag is set when at least 30% of the exertion scores exceed the "high exertion" threshold. The processor may reset (clear) the "excessive movements" flag after the percentage of exertion scores that exceed the "high exertion" threshold drops below 30%, either immediately, after a delay of time, or after a certain quantity of below-threshold exertion scores.

(2) The processor 250 executes instructions for continually receiving and analyzing data collected by a heart-rate physiological sensor 230 and computes a moving average over an averaging interval. The meaning of "continually" is similar to that which is described above. In some embodiments, the averaging interval is 45 seconds. In some embodiments, the processor 250 may cause an alert to be generated and an alert message to be transmitted to an electronic device under the following conditions:

(a) If the heartrate moving average is greater than 145 beats per minute and the "excessive movements" flag is not set; for example, if the individual has been asleep or stationary for the most recent five minutes.

(b) If the heartrate moving average is below 40 beats per minute, regardless of whether the "excessive movements" flag is set.

(c) If the heartrate moving average is greater than 170 beats per minute, the "excessive movements" flag is set, and the individual's detected heartrate is not reducing at a rate of at least six beats per minute over the most recent 60 seconds of detected heartrate data.

In some embodiments, some or all of the above-described thresholds, intervals, delays, quantities, percentages, and sampling rates (collectively referred to as algorithmic parameters) may be adjusted, or customized, by an appropriately permissioned or authorized user or administrator of the cuff 10. Such adjustments may be based on any suitable characteristics of the individual wearing the cuff 10, such as physical or physiological characteristics, and/or based on a location of the individual. Adjusting algorithmic parameters may be accomplished by wirelessly transmitting control messages to the electronics system 210 of the cuff 10.

Figure 7A:
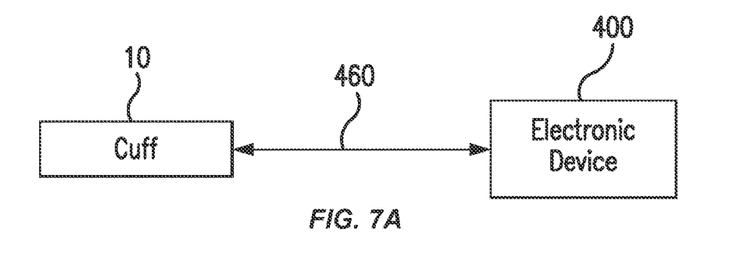
FIGS. 7A-7C show various communications channels between a cuff and an electronic device.
Figure 7B:
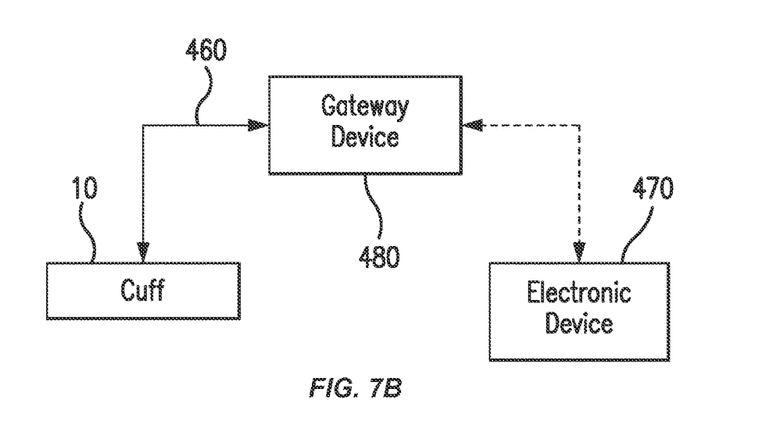
Figure 7C:
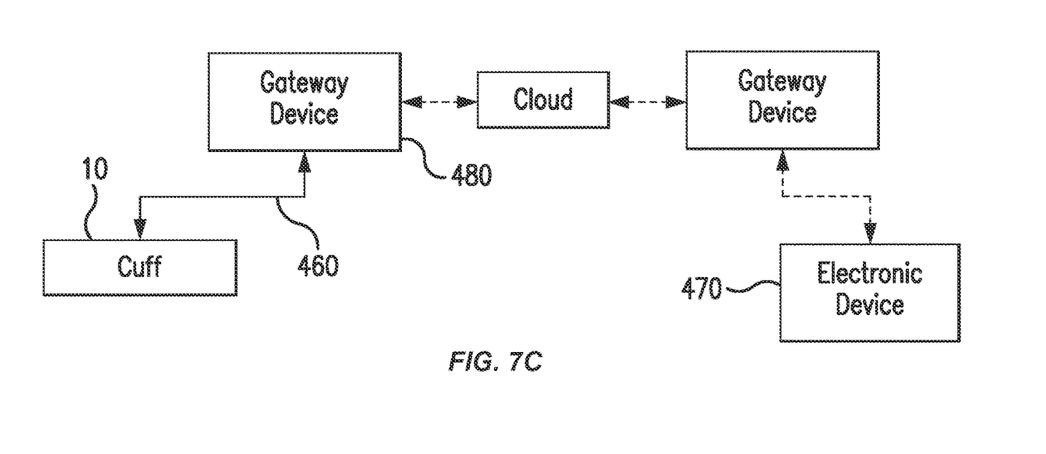

FIGS. 7A-7C show several ways in which data collected by the magnetic sensor 220, the physiological sensor 230, and/or the inertial sensor 240, or alert messages based on such data, may be wirelessly transmitted to an electronic device 400, such as a mobile phone, tablet, laptop computer, connected vehicle, smartwatch, a body-worn multimedia device (such as augmented reality glasses and/or an audio headset), and so on. FIG. 7A depicts a direct wireless transmission from the cuff 10 to the electronic device 470 via a wireless channel 460. Such direct wireless transmission may be achieved by any suitable protocol, for example Bluetooth, Bluetooth Low Energy, ZigBee, Z-Wave, 6LoW-PAN, Thread, ANT & ANT+, DigiMesh, EnOcean, Dash7, WirelessHART, NFC, RFID, and so on. FIGS. 6B and 6C depict the cuff 10 wirelessly transmitting to a gateway device 470, which may be achieved by any suitable protocol, for example any of the protocols listed above, as well as WiFi-ah (HaLow), 2G (GSM), 3G, 4G, LTE (Cat 0, 1, & 3), LTE-M1, NB-IoT, 5G, SigFox, LoRaWAN, Ingenu, Weightless-N, Weightless-P, Weightless-W, and so on. In FIG. 7B, the gateway device 470 relays the transmission to the electronic device 470. In FIG. 7C, the gateway device 470 forwards the transmission to the electronic device via one or more communications networks, for example over the Internet or a cloud network via the TCP/IP protocol. The wireless channel 460 may be unidirectional or bidirectional.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A body-worn cuff, comprising:
 a strap comprising a first end extending from a medial section opposite a second end and adjacent to a third end, wherein the first end and the third end at least partially overlap;
 a catch protruding from a plane of the first end and adapted for insertion through at least one slot in the second end and at least one slot in the third end;
 a housing disposed on the first end that houses an electronics system; and
 a magnet disposed on the third end adjacent to the housing.

2. The cuff of claim 1, wherein the electronics system comprises:
 a battery;
 a processor;
 a wireless transceiver;
 an antenna; and
 a magnetic sensor; wherein
 the processor is configured to cause the wireless transceiver to transmit an alert message via the antenna in response to the magnetic sensor having detected a magnetic field of the magnet that is below a magnitude-threshold.

3. The cuff of claim 1, wherein the electronics system further comprises:
 a physiological sensor configured to detect physiological data of an individual wearing the cuff.

4. The cuff of claim 3, wherein the physiological data pertains to at least one of:
 heartrate;
 blood oxygen saturation; or
 body temperature.

5. The cuff of claim 1, wherein the electronics system further comprises:
 an inertial sensor configured to collect movement data of an individual wearing the cuff.

6. The cuff of claim 5, wherein the inertial sensor is at least one of:
 an accelerometer; or
 a gyroscope.

7. The cuff of claim 1, further comprising:
 a lock adapted to mechanically couple to the catch having been inserted through at least one slot in the second end and at least one slot in the third end.

8. The cuff of claim 2, wherein the electronics system further comprises:
 a heartrate sensor; and
 an accelerometer; wherein
 the processor is configured to cause the wireless transceiver to transmit an alert message via the antenna in response to each of:
 the heartrate sensor having detected a heartrate that is below a first rate-threshold;
 the heartrate having detected a heartrate that is above a second rate-threshold and the accelerometer having detected a first quantity of excessive movements over a movement-interval that does not exceed a movement-threshold; and
 the heartrate sensor having detected a heartrate that is above a third rate-threshold, the accelerometer having detected a second quantity of excessive movements over the movement-interval that exceeds the movement-threshold, and the heartrate sensor having detected a reduction in heartrate that is less than a reduction-threshold amount over a reduction-interval.

9. The cuff of claim 8 wherein at least one parameter as follows is user-configurable:
 the first rate-threshold;
 the second rate-threshold;
 the third rate-threshold;

the reduction-threshold;
the reduction-interval;
the excessive movements;
the movement-interval; and
the movement-threshold.

10. The cuff of claim 2 wherein the alert message is formatted to be transmitted to an electronic device comprising at least one of:
a mobile phone, a computer, a tablet, a vehicle, a wristwatch, or a body-worn multimedia device.

11. A method for monitoring an individual via a body-worn cuff, the method comprising:
engaging the cuff to an appendage of the individual, wherein the cuff comprises:
a strap comprising a first end extending from a medial section opposite a second end and adjacent to a third end, wherein the first end and the third end at least partially overlap;
a catch protruding from a plane of the first end and adapted for insertion through at least one slot in the second end and at least one slot in the third end;
a housing disposed on the first end that houses an electronics system; and
a magnet disposed on the third end adjacent to the housing.

12. The method of claim 11, wherein the electronics system comprises:
a battery;
a processor;
a wireless transceiver;
an antenna; and
a magnetic sensor; wherein
the processor is configured to cause the wireless transceiver to transmit an alert message via the antenna in response to the magnetic sensor having detected a magnetic field of the magnet that is below a magnitude-threshold.

13. The method of claim 11, wherein the electronics system further comprises:
a physiological sensor configured to detect physiological data of an individual wearing the cuff.

14. The method of claim 13, wherein the physiological data pertains to at least one of:
heartrate;
blood oxygen saturation; or
body temperature.

15. The method of claim 11, wherein the electronics system further comprises:
an inertial sensor configured to collect movement data of an individual wearing the cuff.

16. The method of claim 15, wherein the inertial sensor is at least one of:
an accelerometer; or
a gyroscope.

17. The method of claim 11, wherein the cuff further comprises:
a lock adapted to mechanically couple to the catch having been inserted through at least one slot in the second end and at least one slot in the third end.

18. The method of claim 12, wherein the electronics system further comprises:
a heartrate sensor; and
an accelerometer; wherein
the processor is configured to cause the wireless transceiver to transmit an alert message via the antenna in response to each of:
the heartrate sensor having detected a heartrate that is below a first rate-threshold;
the heartrate having detected a heartrate that is above a second rate-threshold and the accelerometer having detected a first quantity of excessive movements over a movement-interval that does not exceed a movement-threshold; and
the heartrate sensor having detected a heartrate that is above a third rate-threshold, the accelerometer having detected a second quantity of excessive movements over the movement-interval that exceeds the movement-threshold, and the heartrate sensor having detected a reduction in heartrate that is less than a reduction-threshold amount over a reduction-interval.

19. The method of claim 18 wherein at least one parameter as follows is user-configurable:
the first rate-threshold;
the second rate-threshold;
the third rate-threshold;
the reduction-threshold;
the reduction-interval;
the excessive movements;
the movement-interval; and
the movement-threshold.

20. The method of claim 12 wherein the alert message is formatted to be transmitted to an electronic device comprising at least one of:
a mobile phone, a computer, a tablet, a vehicle, a wristwatch, or a body-worn multimedia device.

* * * * *